United States Patent
Kubota et al.

(10) Patent No.: US 10,145,766 B2
(45) Date of Patent: Dec. 4, 2018

(54) SMEAR PREPARING APPARATUS

(71) Applicant: SYSMEX CORPORATION, Kobe-shi, Hyogo (JP)

(72) Inventors: Shogo Kubota, Kobe (JP); Seiya Shinabe, Kobe (JP); Kenji Kondo, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 3 days.

(21) Appl. No.: 15/604,698

(22) Filed: May 25, 2017

(65) Prior Publication Data

US 2017/0261412 A1    Sep. 14, 2017

Related U.S. Application Data

(63) Continuation of application No. PCT/JP2015/082501, filed on Nov. 19, 2015.

(30) Foreign Application Priority Data

Nov. 26, 2014   (JP) .................................. 2014-239038

(51) Int. Cl.
| | |
|---|---|
| *G01N 1/00* | (2006.01) |
| *G01N 1/28* | (2006.01) |
| *G01N 1/30* | (2006.01) |
| *G01N 33/48* | (2006.01) |
| *G01N 1/31* | (2006.01) |
| *F26B 9/00* | (2006.01) |
| *F26B 3/04* | (2006.01) |
| *F26B 25/06* | (2006.01) |

(52) U.S. Cl.
CPC ............. *G01N 1/2813* (2013.01); *F26B 3/04* (2013.01); *F26B 9/003* (2013.01); *F26B 25/06* (2013.01); *G01N 1/28* (2013.01); *G01N 1/30* (2013.01); *G01N 1/312* (2013.01); *G01N 33/48* (2013.01); *G01N 2001/302* (2013.01)

(58) Field of Classification Search
CPC ....................................................... G01N 1/00
See application file for complete search history.

(56) References Cited

U.S. PATENT DOCUMENTS

| | | |
|---|---|---|
| 2,257,394 A | 9/1941 | Niersbach |
| 2,623,301 A | 12/1952 | Weiskopf |

(Continued)

FOREIGN PATENT DOCUMENTS

| | | |
|---|---|---|
| JP | S60-171431 A | 9/1985 |
| JP | S61-173062 U | 10/1986 |

(Continued)

*Primary Examiner* — Jyoti Nagpaul
(74) *Attorney, Agent, or Firm* — Metrolexis Law Group, PLLC (57) ABSTRACT

A smear preparing apparatus of an embodiment includes: a transportation part that holds and transports a microscope slide; a housing defining a room therein, the housing including: an insertion opening through which the microscope slide transported by the transportation part is to be inserted, and a feed opening through which air is to be fed; and a blower configured to feed the air through the feed opening to the microscope slide housed in the housing. The housing further includes a discharge opening through which the air fed from the blower through the feed opening is discharged.

20 Claims, 9 Drawing Sheets

(56) References Cited

U.S. PATENT DOCUMENTS

| | | | |
|---|---|---|---|
| 3,701,201 | A | 10/1972 | Drury |
| 5,215,718 | A | 6/1993 | Katzer et al. |
| 5,766,549 | A * | 6/1998 | Gao .................... G01N 1/2813 |
| | | | 118/100 |
| 6,268,208 | B1 | 7/2001 | Kondo |
| 7,297,311 | B2 * | 11/2007 | Tamura ................ G01N 1/2813 |
| | | | 422/519 |
| 2009/0110597 | A1 * | 4/2009 | Ljungmann ............ G01N 1/312 |
| | | | 422/62 |

FOREIGN PATENT DOCUMENTS

| | | |
|---|---|---|
| JP | H03-033655 A | 2/1991 |
| JP | H11-237323 A | 8/1999 |
| JP | 2005-181245 A | 7/2005 |
| JP | 2009-162784 A | 7/2009 |

\* cited by examiner

SMEAR PREPARING APPARATUS

CROSS REFERENCE TO RELATED APPLICATIONS

This application is a continuation application of International Application No. PCT/JP2015/082501, filed on Nov. 19, 2015, entitled "SMEAR PREPARING APPARATUS", which claims priority based on the Article 8 of Patent Cooperation Treaty from prior Japanese Patent Applications No. 2014-239038, filed on Nov. 26, 2014, the entire contents of which are incorporated herein by reference.

TECHNICAL FIELD

The disclosure relates to a smear preparing apparatus.

BACKGROUND ART

Japanese Patent Application Publication No. 2009-162784 (Patent Literature 1) has disclosed a smear preparing apparatus including a fan and a cassette transportation part for transporting a cassette with microscope slides inserted therein. In the cassette, microscope slides with a sample smeared thereon are inserted. The cassette includes an insertion opening at an upper end portion for inserting the microscope slides from above. The fan is provided for drying the microscope slides inserted in the cassette.

In the smear preparing apparatus in Patent Literature 1, there has been a problem that it takes time to dry the microscope slides.

SUMMARY

One or more embodiments of a smear preparing apparatus may include: a transportation part that holds and transports a microscope slide; a housing defining a room therein, the housing including: an insertion opening through which the microscope slide transported by the transportation part is to be inserted, and a feed opening through which air is to be fed; and a blower configured to feed the air through the feed opening to the microscope slide housed in the housing, wherein the housing further includes a discharge opening through which the air fed from the blower through the feed opening is discharged.

DESCRIPTION OF EMBODIMENTS

Hereinafter, an embodiment is described with the drawings.

With reference to FIGS. 1 to 6, descriptions are provided for the structure of smear preparing apparatus 10 according to the embodiment.

[Overview of Smear Preparing Apparatus]

Smear preparing apparatus 10 is an apparatus for automatically preparing a smear by drying microscope slide 900 with a sample subjected to dyeing. The sample is, for example, blood.

[Overview of Dryer Mechanism]

Figure 1:
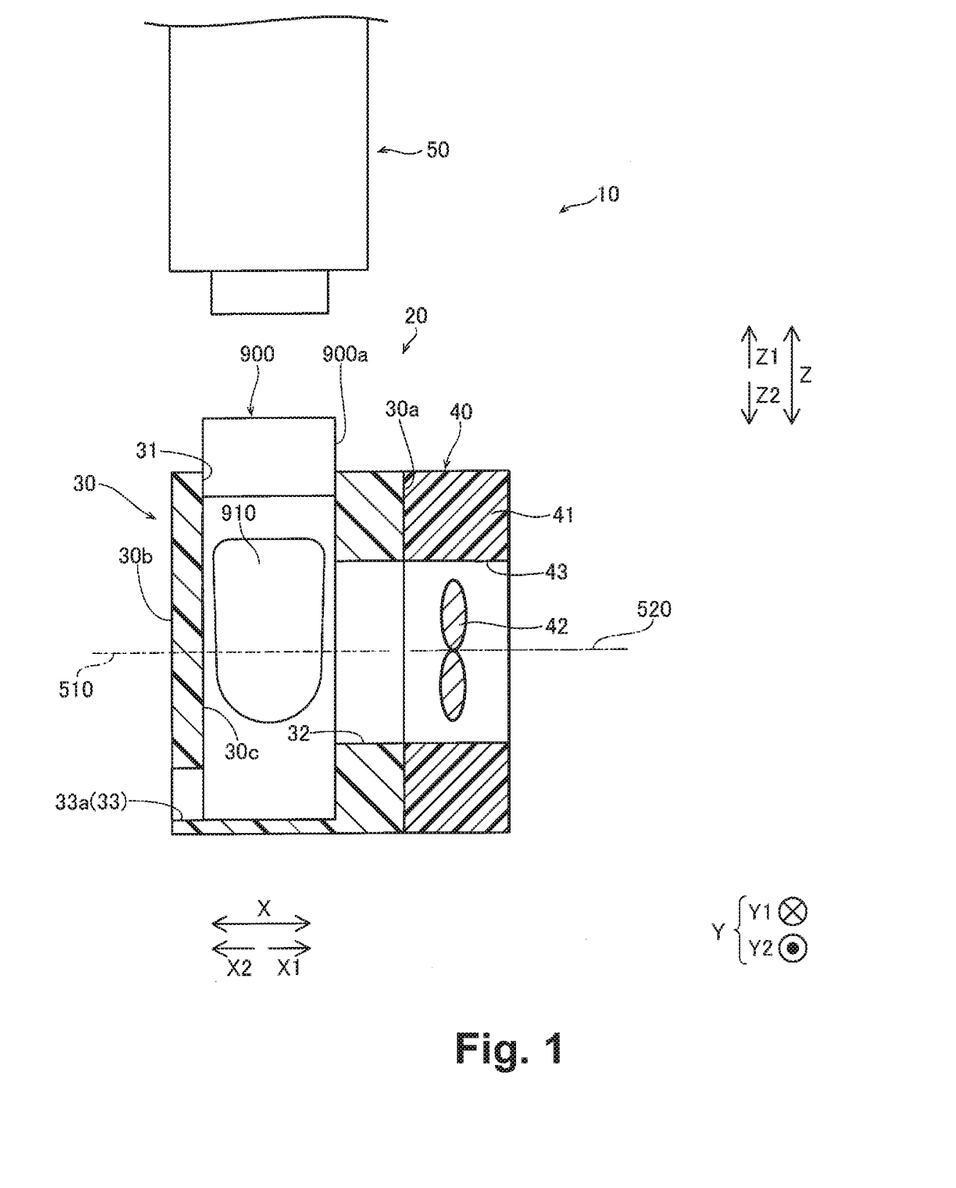
FIG. 1 is a schematic diagram illustrating an outline of a dryer mechanism in a smear preparing apparatus according to one or more embodiments.

As illustrated in FIG. 1, smear preparing apparatus 10 includes dryer mechanism 20 and transportation part 50. Dryer mechanism 20 includes housing 30 and blower 40. Dryer mechanism 20 is provided for drying microscope slide 900 after microscope slide 900 is subjected to a dyeing process and a cleaning process described later.

Housing 30 is provided for housing microscope slide 900. Housing 30 is a box-shaped member having a space or a room inside. Housing 30 includes three openings. Specifically, insertion opening 31 is formed in housing 30 for inserting microscope slide 900 transported by transportation part 50. Feed opening 32 is formed in housing 30 for feeding air. Discharge opening 33 is formed in housing 30 for discharging air fed from blower 40 through feed opening 32.

Insertion opening 31 and discharge opening 33 are arranged to be in an asymmetrical positional relationship with respect to center plane 510 in the up-down direction of housing 30. For the arrangement positions of insertion opening 31 and discharge opening 33, various arrangement positions may be adopted. For example, insertion opening 31 and discharge opening 33 may be arranged in a symmetrical positional relationship with respect to center plane 510 in Z direction of housing 30.

Housing 30 houses microscope slide 900 such that the upper end portion of microscope slide 900 is exposed above the upper end portion of housing 30. For the material for housing 30, various materials may be employed. Resin or metal may be employed for material for housing 30.

Blower 40 includes case 41, fan 42, and fan housing hole 43. Blower 40 is an electric fan capable of forcibly feeding air to the inside of housing 30. Fan 42 is housed in cylindrical fan housing hole 43 to be rotatable about rotation axis 520 parallel to X axis. Blower 40 is provided for feeding air to microscope slide 900 housed in housing 30 through feed opening 32.

Transportation part 50 is arranged above housing 30 and is capable of moving above housing 30. Transportation part 50 is provided for holding and transporting microscope slide 900. Transportation part 50 is provided for taking microscope slide 900 into and out of housing 30 through insertion opening 31.

With the above structure, air fed to the inside of housing 30 by blower 40 can pass to the outside of housing 30 through both insertion opening 31 and discharge opening 33. This makes it possible to pass air effectively inside housing 30. As a result, this reduces the time needed to dry microscope slide 900.

Insertion opening 31 is preferably formed at the upper end portion of housing 30. Microscope slide 900 is inserted into insertion opening 31 from above. In other words, insertion opening 31 faces upward. Feed opening 32 is formed in first side portion 30a of housing 30. Air is fed into housing 30 from X1 side to X2 side through feed opening 32. Discharge opening 33 is formed in second side portion 30b, which is different from first side portion 30a on blower 40 side of housing 30. Note that discharge opening 33 may be formed at the lower end portion of housing 30. This makes it possible to discharge air, fed from feed opening 32, out of discharge opening 33 effectively.

Note that in this specification, the direction in which first side portion 30a is formed in housing 30 corresponds to X1 direction in each figure, and the direction in which second side portion 30b is formed corresponds to X2 direction in each figure. In addition, in this specification, the upward direction corresponds to Z1 direction in each figure, and the downward direction corresponds to Z2 direction in each figure.

More preferably, discharge opening 33 is formed near or at a lower portion of second side portion 30b. This makes it possible to discharge air effectively from both a lower portion and an upper portion of housing 30, using discharge opening 33 and insertion opening 31.

More preferably, discharge opening 33 is formed in second side portion 30b that is provided opposite to first side portion 30a with respect to the room of housing 30. This allows air fed from feed opening 32 to be discharged smoothly from discharge opening 33 without curving complicatedly inside housing 30.

Blower 40 is arranged at a position on first side portion 30a side of housing 30 and feeds air from blower 40 side to housing 30 side. Blower 40 feeds air toward side surface 900a of microscope slide 900 housed in housing 30. Side surface 900a is a surface extending in the thickness direction of microscope slide 900. Blower 40 feeds air toward side surface 900a on X1 side of microscope slide 900.

Preferably, housing 30 is configured such that air fed from blower 40 through feed opening 32 comes into contact with smear portion 910 of microscope slide 900 from the side direction and is discharged from insertion opening 31. A portion of the surface on Y2 side of microscope slide 900 is smear portion 910, on which a sample is smeared. Inside housing 30, microscope slide 900 is housed such that smear portion 910 faces Y2 side. This makes it possible to dry both the surface on smear portion 910 side of microscope slide 900 and the surface on the opposite side from smear portion 910 at the same time. Consequently, this further reduces the time needed for drying, compared to the case where air comes in contact with only one of the surfaces of microscope slide 900. Note that in this specification, the direction orthogonal to the extending direction of rotation axis 20 of fan 42 in blower 40 and parallel to the horizontal direction corresponds to Y direction. X, Y, and Z directions are orthogonal to each other. The surface, on which a sample is smeared, of microscope slide 900 housed in housing 30 is orthogonal to Y axis.

Preferably, discharge opening 33 is formed at a lower portion of second side portion 30b of housing 30, which is provided opposite to first side portion 30a with respect to the room of housing 30. More preferably, discharge opening 33 is formed at lower end portion 33a of housing 30. This prevents difficulty of air passing through near the center in the up-down direction inside housing 30. As a result, it makes it possible to pass air effectively in the entire inside of housing 30.

Preferably, at least part of feed opening 32 is arranged at a position between insertion opening 31 and discharge opening 33 in the up-down direction. This makes it possible to feed air into around the center of the inside of housing 30 and discharge the air from both an upper portion and a lower portion of housing 30 with insertion opening 31 and discharge opening 33.

Preferably, inner wall surface 30c is formed at an area of second side portion that is provided opposite to first side portion 30a with respect to the room of housing 30, of housing 30, the area facing feed opening 32. Blower 40 feeds air from X1 direction toward side surface 900a of microscope slide 900 and inner wall surface 30c on X2 side. This makes it possible to change the direction of the air fed into housing 30 by hitting the air against inner wall surface 30c, and feed the air to insertion opening 31 and discharge opening 33. As a result, it possible to pass air effectively in the housing 30.

Preferably, feed opening 32 is arranged at a position overlapping microscope slide 900, in a direction of the width of microscope slide 900, in the state where microscope slide 900 is housed in housing 30. The widthwise direction of microscope slide 900 is orthogonal to the longitudinal direction of microscope slide 900. Feed opening 32 is arranged at a position overlapping microscope slide 900 housed in housing 30 as viewed in X direction. This makes it possible to directly hit the air fed from blower 40 against side surface 900a of microscope slide 900.

[Detailed Structure of Dryer Mechanism]

Hereinafter, with reference to FIG. 2 and following figures, descriptions are specifically provided for the structure of a preferred embodiment of dryer mechanism 20 illustrated in FIG. 1.

Figure 2:
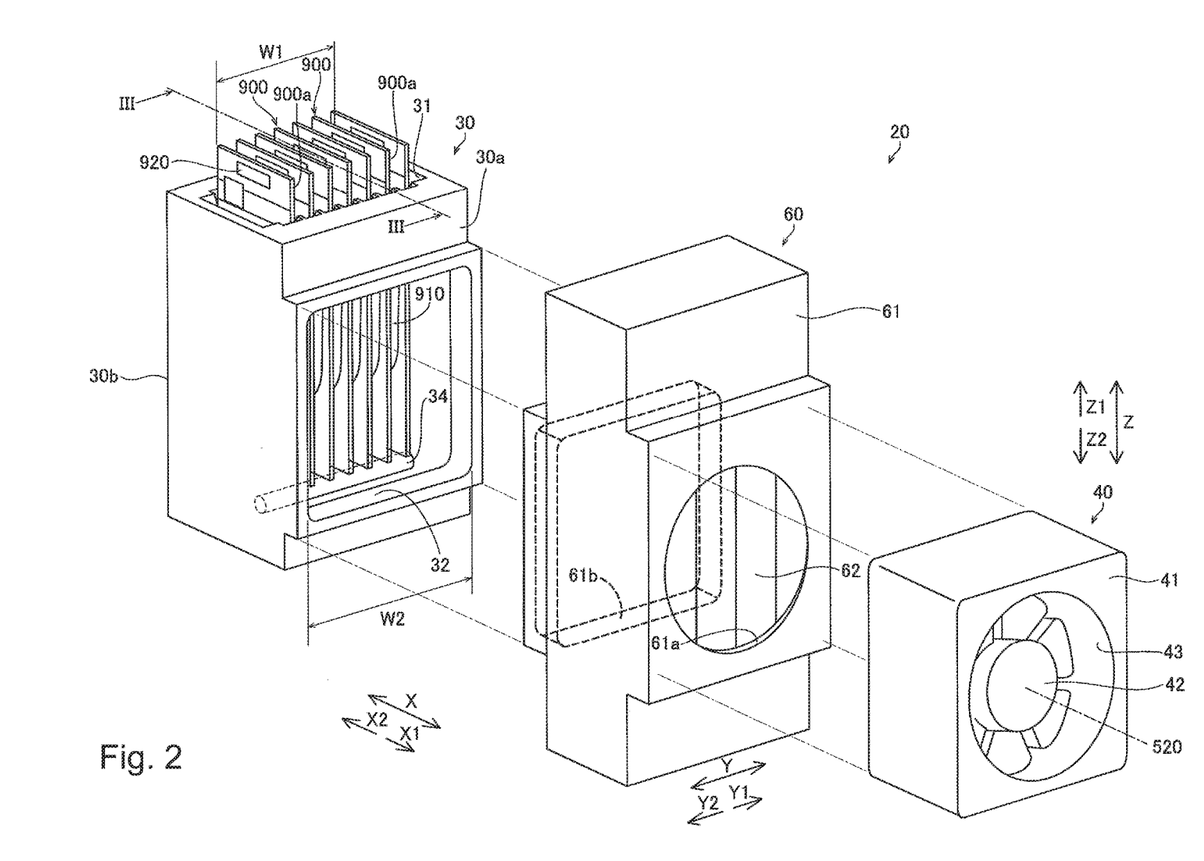
FIG. 2 is an exploded perspective view of a dryer mechanism in a smear preparing apparatus according to one or more embodiments.

In the preferred embodiment, as illustrated in FIG. 2, dryer mechanism 20 includes housing 30, blower 40, and heater 60.

Housing 30 is configured to house multiple microscope slides 900. Housing 30 is capable of housing seven microscope slides 900 along Y direction. In housing 30, microscope slide 900 is housed such that the surface of smear portion 910 side faces Y2 side.

The number of microscope slides 900 that can be housed is not particularly limited. Housing 30 may be configured to house one to six microscope slides 900, or eight or more microscope slides 900.

Insertion opening 31 is configured such that microscope slides 900 can be inserted in housing 30 in the state where microscope slides 900 are apart from each other in Y direction. Insertion opening 31 is formed in the shape of comb teeth in plan view.

Feed opening 32 is formed roughly in a rectangular shape. Feed opening 32, preferably, has a width W2 which is wider than distance W1 between microscope slide 900 at one end and microscope slide 900 at the other end in the direction in which microscope slides 900 are arranged in the state where microscope slides 900 are housed in housing 30. In other words, parts of all of microscope slides 900 are provided in feed opening 32 as seen from X direction. This makes it possible to hit the air fed from blower 40 against all the microscope slides 900 housed in housing 30. As a result, all the microscope slides 900 can be dried uniformly.

Preferably, housing 30 includes shaft 34 to support lower end portions of housed microscope slides 900. Shaft 34 is a bar-shaped member extending in Y direction from the inner surface on Y1 side to the inner surface on Y2 side of housing 30. Shaft 34 is arranged away from bottom surface 30e of housing 30 and parallel to bottom surface 30e (see FIG. 3).

Shaft 34 supports each microscope slide 900 from below to be in line contact with each microscope slide 900 housed in housing 30. This makes a space below microscope slides 900. As a result, it is possible to pass air effectively.

For the structure to support the lower end portions of microscope slides 900, various structure can be adopted besides shaft 34. For example, microscope slides 900 may be supported by forming, at bottom surface 30e (see FIG. 3) of housing 30, a support portion that supports the lower end portions of microscope slides 900.

Preferably, heater 60 is arranged between blower 40 and feed opening 32 of housing 30. Heater 60 is sandwiched between blower 40 and housing 30. The air fed from blower 40 receives heat when passing through heater 60 and is fed into housing 30 in the state of warm air. This further reduces the time needed to dry microscope slides 900.

Specifically, heater 60 includes case 61 and heat generation portion 62. Case 61 includes hole 61a on blower 40 side and hole 61b on housing 30 side. Heat generation portion 62 is housed in case 61. Heat generation portion 62 connects with the outside of case 61 through holes 61a and 61b.

Hole 61a has a circular shape as viewed from X direction. Hole 61a is arranged at a position corresponding to fan housing hole 43 of blower 40 as viewed from Y direction. Hole 61a is arranged to overlap with fan housing hole 43 of blower 40 as viewed from X1 direction. Hole 61b has a rectangular shape as viewed from X direction. Hole 61b is arranged at a position corresponding to feed opening 32 of housing 30 as viewed from Y direction. Hole 61b is arranged to overlap with feed opening 32 of housing 30 as viewed from X1 direction.

Figure 3:
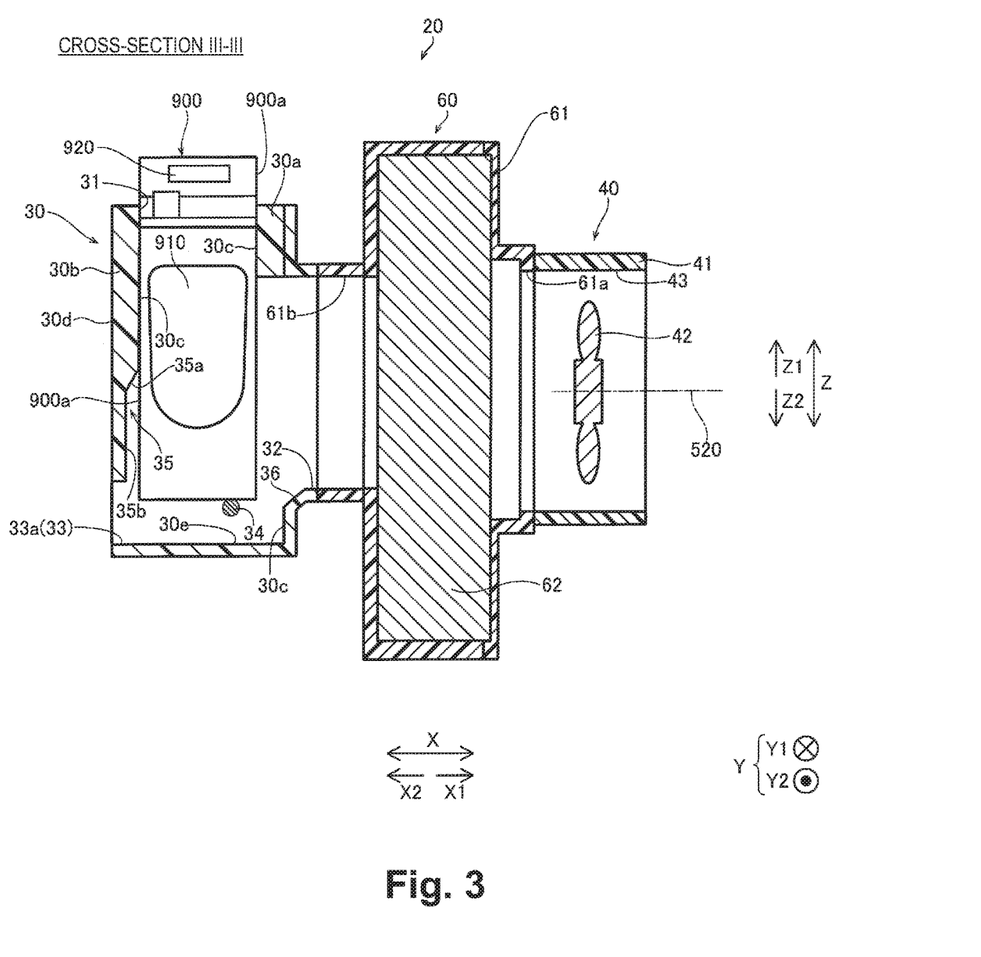
FIG. 3 is a cross-sectional view taken along line III-III in FIG. 2.

As illustrated in FIG. 3, preferably, a lower portion of inner wall surface 30c on X2 side of housing 30 includes recess 35 which is recessed in the direction from inner wall surface 30c to outer wall surface 30d. In other words, the thickness or the distance between inner wall surface 30c and outer wall surface 30d of second side portion 30b at recess 35 is thinner than that of second side portion 30b other than recess 35. A lower end portion of recess 35 is adjacent to discharge opening 33. Recess 35 is at a position away from side surfaces 900a of microscope slides 900 in the state where microscope slides 900 are housed in housing 30. In other words, recess 35 does not come in contact with side surfaces 900a of microscope slide 900. With this structure, inner wall surface 30c and side surfaces 900a of microscope slide 900 do not come in contact with each other, unlike the structure without recess 35. As a result, it is possible to hit air against side surfaces 900a of microscope slides 900 which faces recess 35.

More preferably, recess 35 is formed at a lower end portion of inner wall surface 30c. Upper portion 35a of recess 35 is inclined in the downward direction as viewed from Y direction. Portion 35b other than upper portion 35a of recess 35 is formed in parallel to side surfaces 900a of microscope slides 900 housed in housing 30, as viewed from Y direction.

In addition, preferably, housing 30 includes inclined portion 36 on inner wall surface 30c on X1 side of first side portion 30a. Inclined portion 36 is inclined in the downward direction such that the air fed from blower 40 through feed opening 32 is guided toward discharge opening 33. This makes it possible to pass air effectively inside housing 30.

More preferably, inclined portion 36 is formed at a position away from microscope slides 900. Inclined portion 36 is arranged to overlap with discharge opening 33 as viewed from X2 direction.

Shaft 34 is arranged on X1 side of the center of microscope slides 900 housed in the housing 30 in X direction. Shaft 34 is arranged to overlap with discharge opening 33 as viewed from X direction. The diameter of the cross section of shaft 34 is smaller than the length of discharge opening 33 in Z direction, as viewed from Y direction.

Figure 4:
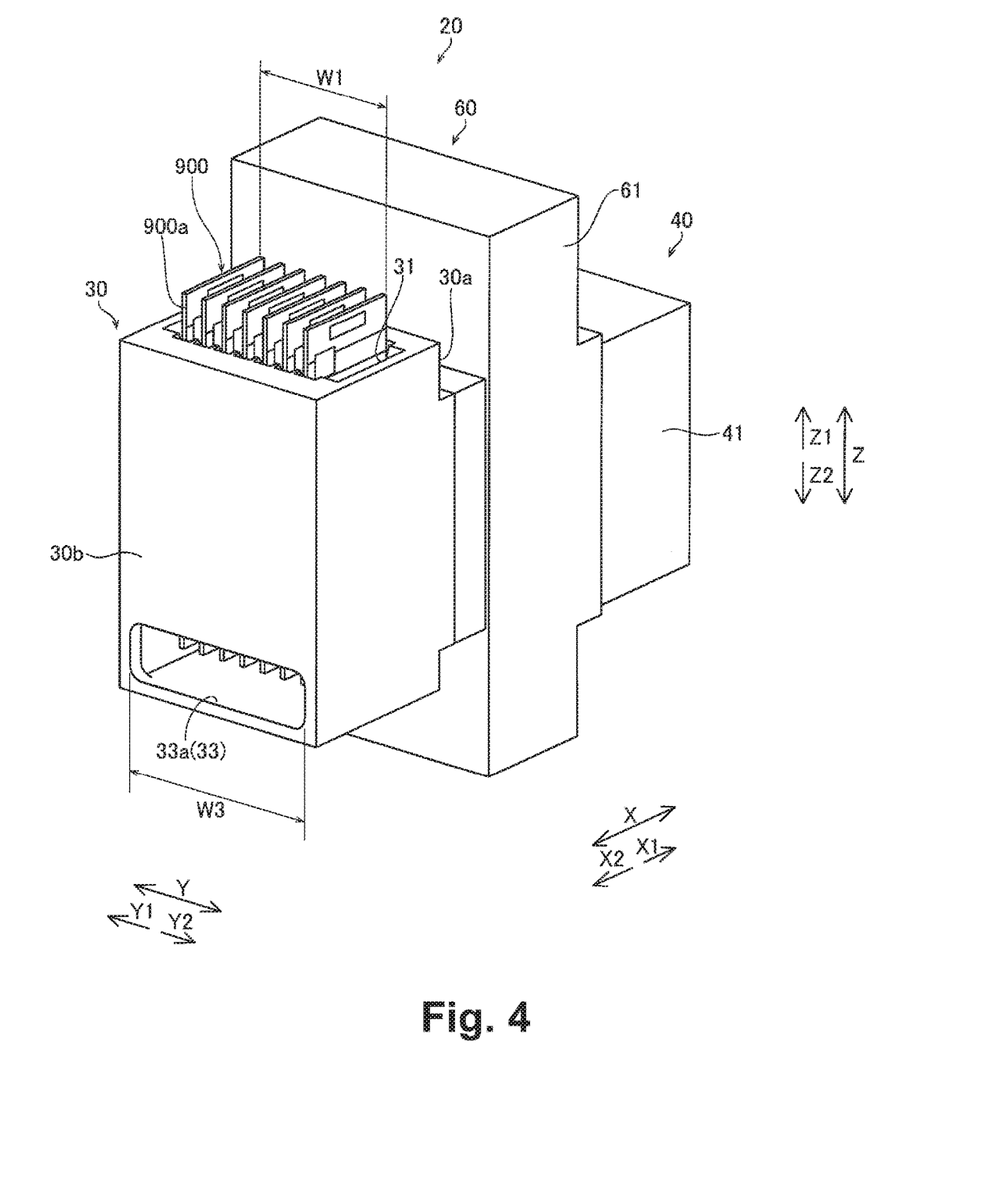
FIG. 4 is a perspective view as viewed from X2 side of a dryer mechanism in a smear preparing apparatus according to one or more embodiments.

As illustrated in FIG. 4, preferably, discharge opening 33 is formed at a position that allows lower end portions of microscope slides 900 to be exposed, in the state where microscope slides 900 are housed in housing 30. In other words, the lower end portions of all of microscope slides 900 are provided in discharge opening 33 as seen from X direction. This makes it possible to form an area where air flow speed is high at the lower end portions of microscope slides 900 as illustrated in the simulation result described later (see FIG. 9). As a result, it is possible to dry the lower end portions of microscope slides 900 effectively.

Preferably, discharge opening 33 has a rectangular shape as viewed from X direction. Discharge opening 33 has width W3, which is wider than distance W1 between microscope slide 900 at one end and microscope slide 900 at the other end in Y direction in the state where microscope slides 900 are housed in housing 30. This makes it possible to discharge air through discharge opening 33 from the area where all the microscope slides 900 housed in housing 30 are arranged.

The opening area of discharge opening 33 is almost the same as that of insertion opening 31 in the state where seven microscope slides 900 are housed in housing 30. In the state where seven microscope slides 900 are housed in housing 30, the amount of air discharged from discharge opening 33 is substantially the same as that discharged from insertion opening 31. This makes it possible to discharge air from discharge opening 33 and insertion opening 31 in a well-balanced manner.

Each of the opening areas of discharge opening 33 and insertion opening 31 is smaller than that of feed opening 32. This makes large the flow speeds of the air discharged from discharge opening 33 and insertion opening 31.

[Structure of Main Portions of Smear Preparing Apparatus]

Figure 5:
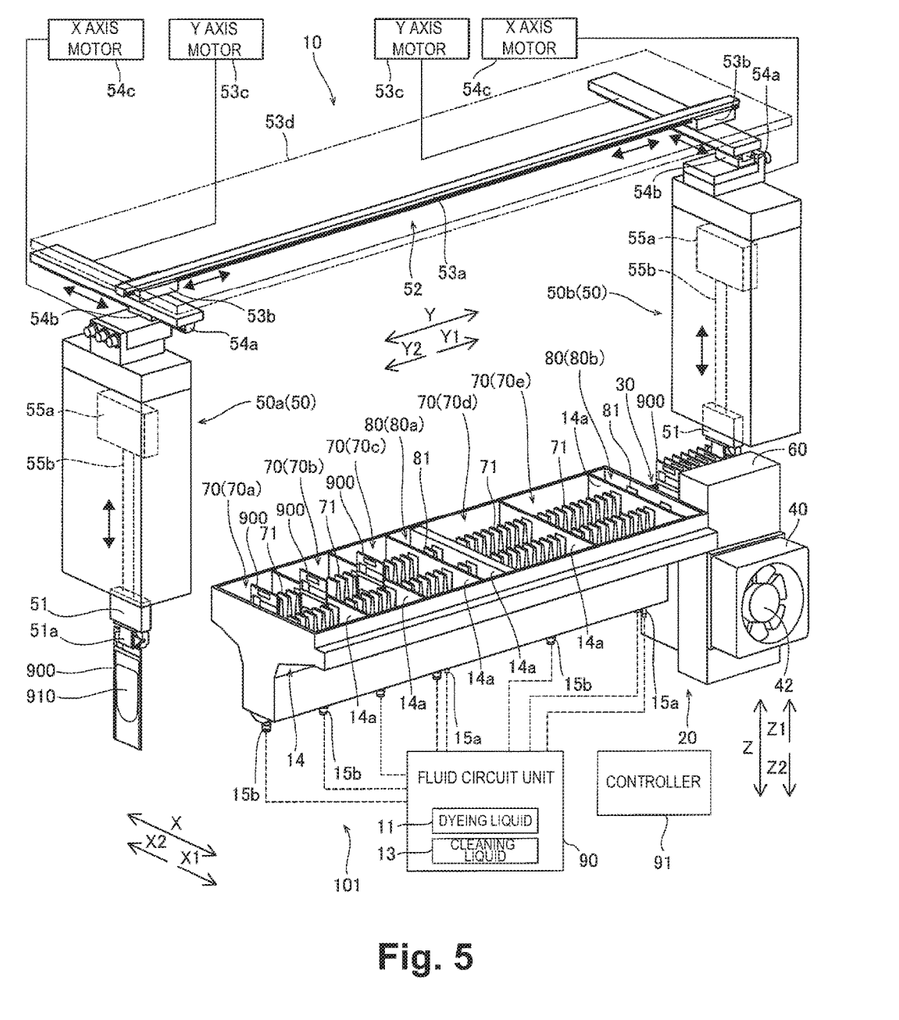
FIG. 5 is a perspective view illustrating transportation parts, dyeing tubs, cleaning tubs, and a dryer mechanism of a smear preparing apparatus according to one or more embodiments.

As illustrated in FIG. 5, smear preparing apparatus 10 includes dyeing unit 101 that performs a dyeing process, a cleaning process, and a drying process on smeared samples. Dyeing unit 101 includes dryer mechanism 20, transportation part 50, dyeing tubs 70, cleaning tubs 80, fluid circuit unit 90, and controller 91. Dyeing tubs 70 includes first dyeing tub 70a, second dyeing tub 70b, third dyeing tub 70c, fourth dyeing tub 70d, and fifth dyeing tub 70e. First dyeing tub 70a can store first dyeing liquid. Second dyeing tub 70b can store second dyeing liquid. Third dyeing tub 70c can store third dyeing liquid. Fourth dyeing tub 70d and fifth dyeing tub 70e can store fourth dyeing liquid. Cleaning tubs 80 includes first cleaning tub 80a and second cleaning tub 80b partitioned by partition members 14a. This makes it possible to transport microscope slides 900 subjected to the dyeing process with dyeing tubs 70 to dryer mechanism 20 provided in the same apparatus and perform a drying process promptly.

Alternatively, various structures may be adopted for smear preparing apparatus 10. For example, although in smear preparing apparatus 10, a smearing process is further performed, in which a sample is smeared on microscope slide 900, as an upstream process of the dyeing process, smear preparing apparatus 10 may be configured such that a smearing process is not performed.

Transportation part 50 is provided for holding and transporting microscope slides 900 with sample smeared thereon. Transportation part 50 includes first transportation part 50a and second transportation part 50b. Both first transportation part 50a and second transportation part 50b of transportation part 50 are arranged above dyeing tubs 70 and cleaning tubs 80. Each of first transportation part 50a and second transportation part 50b is capable of moving in X direction and Y direction by movement mechanism 52.

Movement mechanism 52 includes Y axis rail 53a and Y axis sliders 53b for Y direction, X axis rails 54a and X axis sliders 54b for X direction, and Y axis motors 53c and X axis motors 54c. For X axis motor 54c and Y axis motor 53c, for example, stepping motors or servo motors can be employed.

Y axis rail 53a extends linearly in Y direction and is fixed on the lower surface of support member 53d. Support member 53d is a ceiling portion, a support beam member, or the like of a case of smear preparing apparatus 10. Y axis slider 53b is attached on Z2 side of Y axis rail 53a and capable of moving along Y axis rail 53a. Y axis motor 53c moves Y axis slider 53b in Y direction by means of an unillustrated transmission mechanism.

X axis rail 54a extends linearly in X direction and is fixed on the lower surface of Y axis slider 53b. X axis slider 54b is attached on Z2 side of X axis rail 54a and capable of moving along X axis rail 54a. X axis motor 54c moves X axis slider 54b in X direction by means of an unillustrated transmission mechanism.

Y axis sliders 53b, X axis rails 54a, X axis sliders 54b, X axis motors 54c, and Y axis motors 53c each are provided in pairs. First transportation part 50a and second transportation part 50b are attached on lower face sides of the pair of X axis sliders 54b, respectively. This enables first transportation part 50a and second transportation part 50b to move in X direction along the respective X axis rails 54a independently of each other. In addition, first transportation part 50a and second transportation part 50b are capable of moving in Y direction along common Y axis rail 53a independently of each other.

First transportation part 50a and second transportation part 50b have a common structure. Each of first transportation part 50a and second transportation part 50b includes Z axis motor 55a and transmission mechanism 55b for lifting hand 51 up and down. Z axis motor 55a lifts hand 51 up and down by means of transmission mechanism 55b.

Hand 51 is capable of holding one microscope slide 900. Hand 51 holds microscope slide 900 by pinching microscope slide 900 in the thickness direction with a pair of hold plates 51a.

First transportation part 50a can move to a position above each of first dyeing tub 70a, second dyeing tub 70b, third dyeing tub 70c, and first cleaning tub 80a, which are on Y2 side. First transportation part 50a is capable of inserting and pulling microscope slide 900 one by one into and out of each of first dyeing tub 70a, second dyeing tub 70b, third dyeing tub 70c, and first cleaning tub 80a described later.

Second transportation part 50b can move to a position above each of second cleaning tub 80b, fifth dyeing tub 70e, fourth dyeing tub 70d, and first cleaning tub 80a, which are on Y1 side, a position above dryer mechanism 20, and a position at storage part 106 (see FIG. 6) described later. Thus, second transportation part 50b is capable of inserting and pulling microscope slide 900 one by one into and out of each of fourth dyeing tub 70d and fifth dyeing tub 70e as well as first cleaning tub 80a and second cleaning tub 80b.

First transportation part 50a and second transportation part 50b each are capable of transporting different microscope slides 900 in parallel. Movement ranges of first transportation part 50a and second transportation part 50b are overlapped with each other at first cleaning tub 80a. Hence, handover of microscope slide 900 is performed at first cleaning tub 80a.

Second transportation part 50b transports sequentially microscope slides 900 on which dyeing is completed, from dyeing tub 70 to housing 30 one by one. This makes it possible to transport microscope slides 900 on which the dyeing process is completed sequentially to dryer mechanism 20.

Specifically, second transportation part 50b transports microscope slide 900 to housing 30 via each dyeing tub 70 and each cleaning tub 80. Second transportation part 50b transports microscope slide 900 one by one into housing 30 through insertion opening 31.

Second transportation part 50b sequentially pulls microscope slide 900 out of housing 30 one by one and transports it to storage part 106 (see FIG. 6) in the order from microscope slide 900 on which drying is completed after a specified time has passed. This makes it possible to transport microscope slides 900 on which drying process is completed, to storage part 106 sequentially, which improves the process efficiency of the dyeing process.

Dyeing tub 70 is provided for storing dyeing liquid 11 so that microscope slides 900 with a sample smeared can be soaked. Dyeing tub 70 is a container capable of storing dyeing liquid 11 therein. Dyeing tub 70 includes first holders 71 configured to hold microscope slides 900. Microscope slides 900 inserted in dyeing tub 70 are arranged along Y direction. The dyeing process is performed in dyeing tub 70 by soaking microscope slides 900 held by first holders 71 in dyeing liquid 11 for a specified time.

Cleaning tub 80 is provided for storing cleaning liquid 13 so that microscope slides 900 can be soaked therein. Cleaning tub 80 includes second holders 81, which are similar to first holders 71 of dyeing tub 70. Other structure of cleaning tub 80 is common to the structure of dyeing tub 70.

Five dyeing tubs 70 of first dyeing tub 70a to fifth dyeing tub 70e and two cleaning tubs 80 of first cleaning tub 80a and second cleaning tub 80b are integrally formed as single structure 14 in the state where each tub is partitioned by partition members 14a. At a position on Y1 direction side of second cleaning tub 80b, dryer mechanism 20 is arranged to be adjacent to structure 14.

Each dyeing tub 70 and each cleaning tub 80 are arranged in the order of, from Y2 side, first dyeing tub 70a, second dyeing tub 70b, third dyeing tub 70c, first cleaning tub 80a, fourth dyeing tub 70d, fifth dyeing tub 70e, and second cleaning tub 80b. Microscope slide 900 is transported from first dyeing tub 70a on Y2 side to each tab sequentially and processed by being soaked in dyeing liquid 11 or cleaning liquid 13 stored in each tab for a specified set time. Each of dyeing tubs 70 and cleaning tubs 80 is separately provided with supply port 15a for supplying liquid and discharge port 15b for discharging the liquid.

Fluid circuit unit 90 supplies each dyeing tub 70 with dyeing liquid 11 through supply port 15a. Fluid circuit unit 90 supplies each cleaning tub 80 with cleaning liquid 13 through supply port 15a. Fluid circuit unit 90 discharges dyeing liquid 11 from each dyeing tub 70 through discharge port 15b. Fluid circuit unit 90 discharges cleaning liquid 13 from each cleaning tub 80 through discharge port 15b.

Controller 91 performs controlling transportation part 50, dryer mechanism 20, and the like. Controller 91 includes an unillustrated CPU and memory. Preferably, controller 91 controls operation of blower 40 on the basis of the housing state of microscope slides 900 in housing 30. This allows blower 40 to be driven only when microscope slides 900 need drying. Accordingly, power consumption can be reduced.

[Other Structure of Smear Preparing Apparatus]

Figure 6:
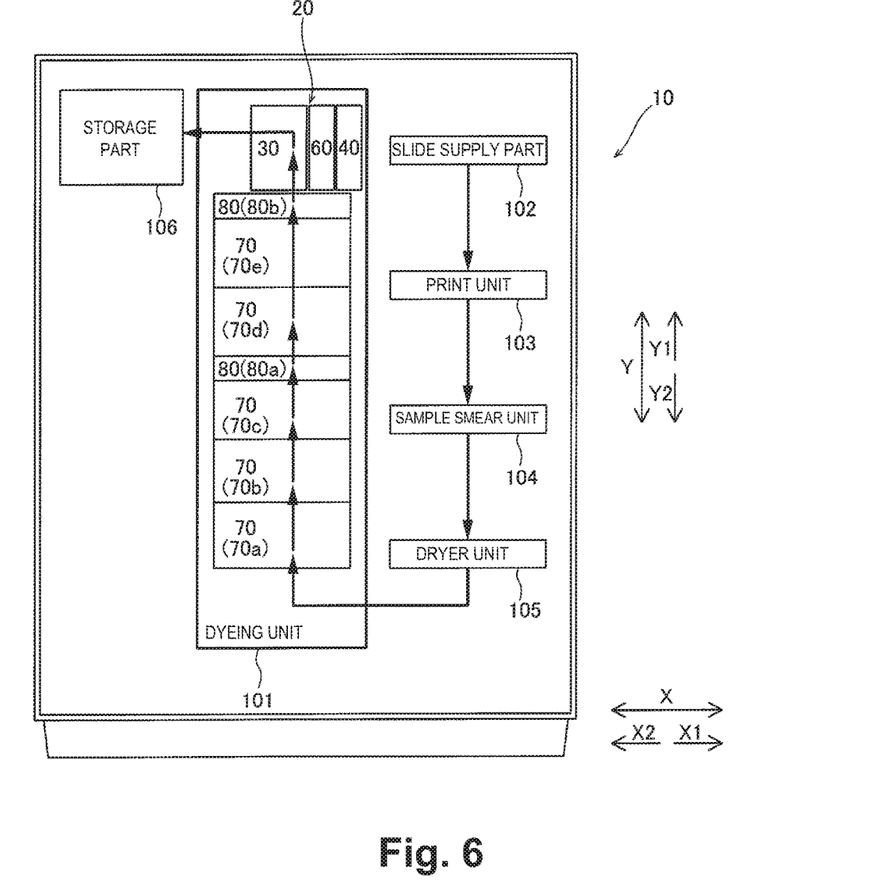
FIG. 6 is a schematic plan view for explaining an overall structure of a smear preparing apparatus according to one or more embodiments.

Next, with reference to FIG. 6, descriptions are provided for other structure of the smear preparing apparatus 10.

In the preferred embodiment, smear preparing apparatus 10 further includes slide supply part 102, print unit 103, sample smear unit 104, dryer unit 105, and storage part 106.

Slide supply part 102 stores a large number of microscope slides 900 (see FIG. 3) in an unused state before a sample is applied. Slide supply part 102 is capable of supplying microscope slide 900 before application to print unit 103 one by one.

Print unit 103 is capable of printing various information such as sample information on frosted portion 920 (see FIG. 3) near the upper end portion of microscope slide 900. Print unit 103 is capable of transporting printed microscope slide 900 to sample smear unit 104.

Sample smear unit 104 is capable of smearing a sample on microscope slide 900. Sample smear unit 104 is capable of sucking a sample with an unillustrated sample suck mechanism and smearing the sample on smear portion 910 (see FIG. 3) of microscope slide 900 transported from print unit 103. Sample smear unit 104 is capable of transporting microscope slide 900 after smearing process to dryer unit 105.

Dryer unit 105 is capable of receiving microscope slide 900 with the sample smeared thereon from sample smear unit 104, and feeding air toward microscope slide 900 to dry smear portion 910. Dryer unit 105 is capable of transporting dried microscope slide 900 to dyeing unit 101.

Dyeing unit 101 is capable of performing the dyeing process on the sample smeared on microscope slide 900. In dyeing unit 101, a dyeing process and a cleaning process are performed in each dyeing tub 70 and each cleaning tub 80. After that, the drying process is performed with dryer mechanism 20. Thereafter, microscope slides 900 already dried are transported to storage part 106 one by one. Transportation of microscope slides 900 between these units is performed by transportation part 50.

Storage part 106 stores the microscope slides that have been dried by blower 40.

With the above structure, smear preparing apparatus 10 performs each process of printing, smearing a sample, and dyeing and drying the sample on microscope slide 900, and automatically prepares smears.

[Dyeing Operation of Smear Preparing Apparatus]

Figure 7:
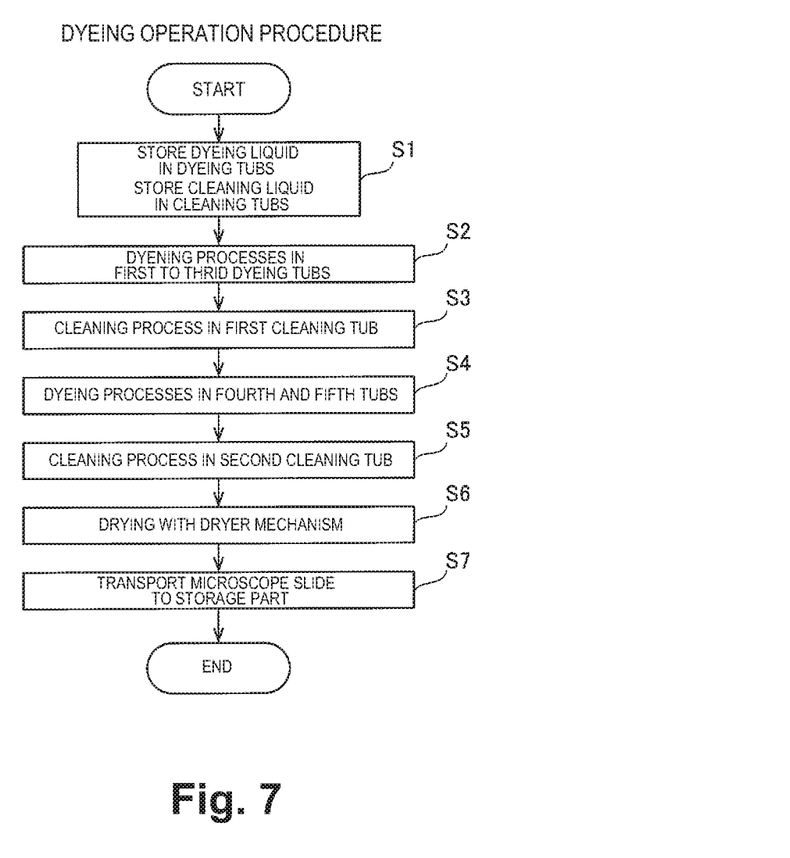
FIG. 7 is a flowchart for explaining dyeing operation of a smear preparing apparatus.

Next, with reference to FIGS. 5 to 7, descriptions are provided for dyeing operation of smear preparing apparatus 10. The process at step S1 is performed by fluid circuit unit 90, and the processes at steps S2 to S7 are performed by controller 91.

At step S1 in FIG. 7, fluid circuit unit 90 performs a process of storing dyeing liquid 11 and cleaning liquid 13 in dyeing tubs 70 and cleaning tubs 80, respectively.

At step S2, transportation part 50 transports microscope slide 900 sequentially to first dyeing tub 70a, second dyeing tub 70b, and third dyeing tub 70c (see FIG. 5), and a dyeing process is performed at each dyeing tub.

Specifically, transportation part 50 transports one microscope slide 900 to first dyeing tub 70a. Transported microscope slide 900 is soaked in first dyeing liquid 11 for a specified set time T1. After that, transportation part 50 transports microscope slide 900 to second dyeing tub 70b and a dyeing process is performed in second dyeing tub 70b for a specified set time T2. Thereafter, transportation part 50 transports microscope slide 900 to third dyeing tub 70c and a dyeing process is performed in third dyeing tub 70c for a specified set time T3.

At step S3, transportation part 50 transports microscope slide 900 to first cleaning tub 80a (see FIG. 5) and performs a cleaning process in first cleaning tub 80a. Specifically, transportation part 50 transports one microscope slide 900 from third dyeing tub 70c to first cleaning tub 80a and performs the cleaning process in first cleaning tub 80a for a specified set time T4.

At step S4, transportation part 50 transports microscope slide 900 to either fourth dyeing tub 70d or fifth dyeing tub 70e (see FIG. 5), and a dyeing process is performed in fourth dyeing tub 70d or fifth dyeing tub 70e to which microscope slide 900 is transported.

Specifically, transportation part 50 transports one microscope slide 900 from first cleaning tub 80a to either fourth dyeing tub 70d or fifth dyeing tub 70e, and soaks the microscope slide 900 in fourth dyeing liquid 11 for a specified set time T5.

At step S5, transportation part 50 transports microscope slide 900 to second cleaning tub 80b (see FIG. 5) and a cleaning process is performed in second cleaning tub 80b. Specifically, transportation part 50 transports one microscope slide 900 from fourth dyeing tub 70d or fifth dyeing tub 70e to second cleaning tub 80b, and the cleaning process is performed in second cleaning tub 80b for a specified set time T6.

At step S6, transportation part 50 transports microscope slide 900 to dryer mechanism 20 (see FIG. 5), and the microscope slide 900 is dried in dryer mechanism 20. Microscope slide 900 is dried in dryer mechanism 20 for a specified set time T7. At this process, the dyeing process of a smear for one microscope slide 900 is completed.

At step S7, transportation part 50 takes out one microscope slide 900, the dyeing process on which has been completed, from dryer mechanism 20 and transports the microscope slide 900 to storage part 106 (see FIG. 6). In the way described above, the dyeing operation of smear preparing apparatus 10 is performed.

[Drying Process]

Figure 8:
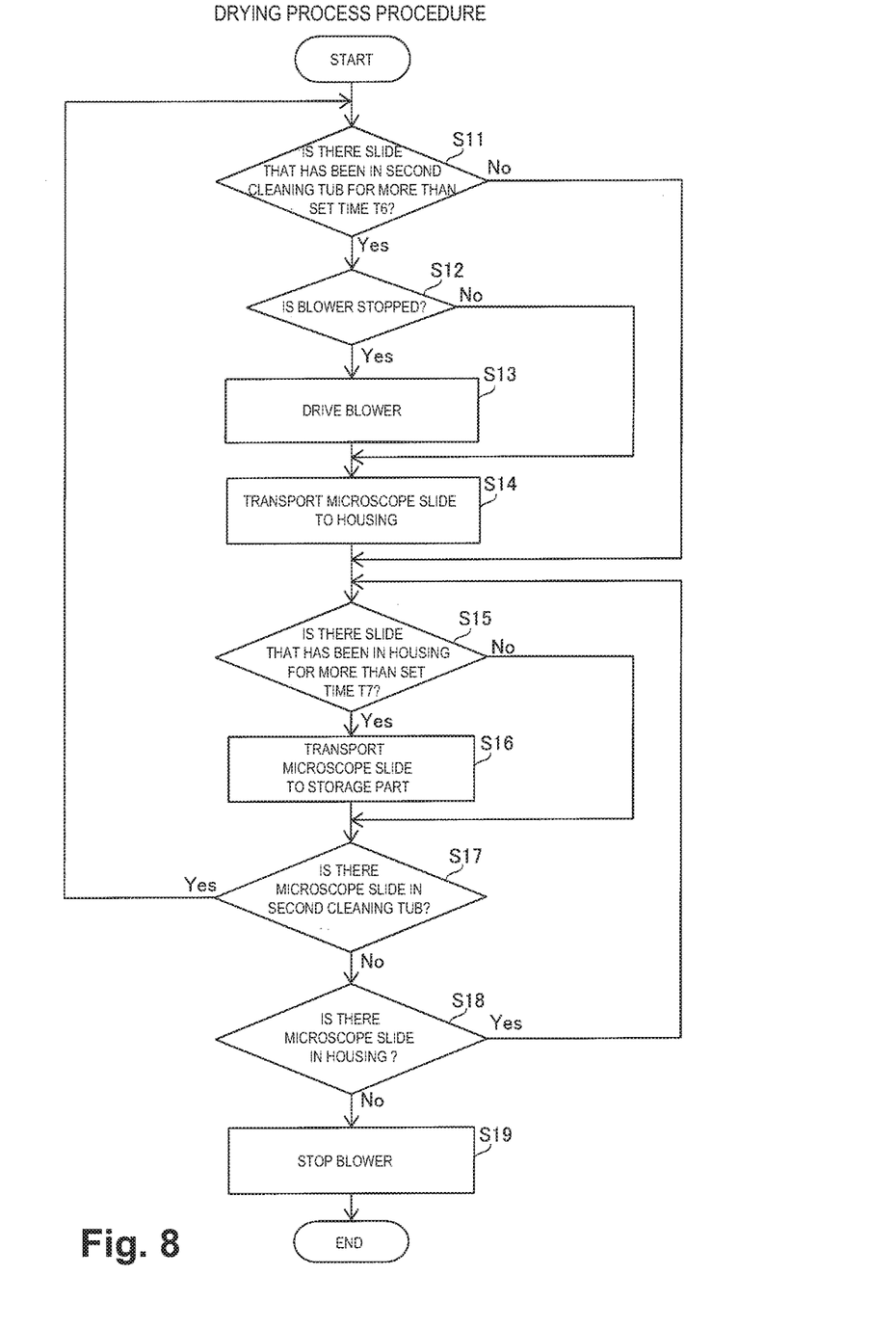
FIG. 8 is a flowchart for explaining a drying process of a smear preparing apparatus.

Next, with reference to FIGS. 5 and 8, descriptions are provided for the drying process. The drying process is performed by controller 91.

At step S11 in FIG. 8, controller 91 determines whether there is microscope slide 900 that has been in second cleaning tub 80b (see FIG. 5) for more than the set time T6. If there is microscope slide 900 that has been in second cleaning tub 80b for more than the set time T6, controller 91 advances the process to step S12. On the other hand, if there is no microscope slide 900 that has been in second cleaning tub 80b for more than the set time T6, controller 91 advances the process to step S15.

At step S12, controller 91 determines whether blower 40 is stopped. If blower 40 is stopped, controller 91 advances the process to step S13. On the other hand, if blower 40 is not stopped, controller 91 advances the process to step S14.

At step S13, controller 91 drives blower 40.

At step S14, controller 91 moves microscope slides 900 from second cleaning tub 80b to housing 30 one by one.

At step S15, controller 91 determines whether there is microscope slide 900 that has been in housing 30 for more than the set time T7. If there is microscope slide 900 that has been in housing 30 for more than the set time T7, controller 91 advances the process to step S16. On the other hand, if there is no microscope slide 900 that has been in housing 30 for more than the set time T7, controller 91 advances the process to step S17.

At step S16, controller 91 moves microscope slides 900 to housing 30.

At step S17, controller 91 determines whether there is microscope slide 900 in second cleaning tub 80*b*. If there is microscope slide 900 in second cleaning tub 80*b*, controller 91 returns the process to step S11. On the other hand, if there is no microscope slide 900 in second cleaning tub 80*b*, controller 91 advances the process to step S18.

At step S18, controller 91 determines whether there is microscope slide 900 in housing 30. If there is microscope slide 900 in housing 30, controller 91 returns the process to step S15. On the other hand, if there is no microscope slide 900 in housing 30, controller 91 advances the process to step S19.

At step S19, controller 91 stops blower 40.

In the way described above, the drying process is performed.

[Simulation Result of Air Flow]

Figure 9:
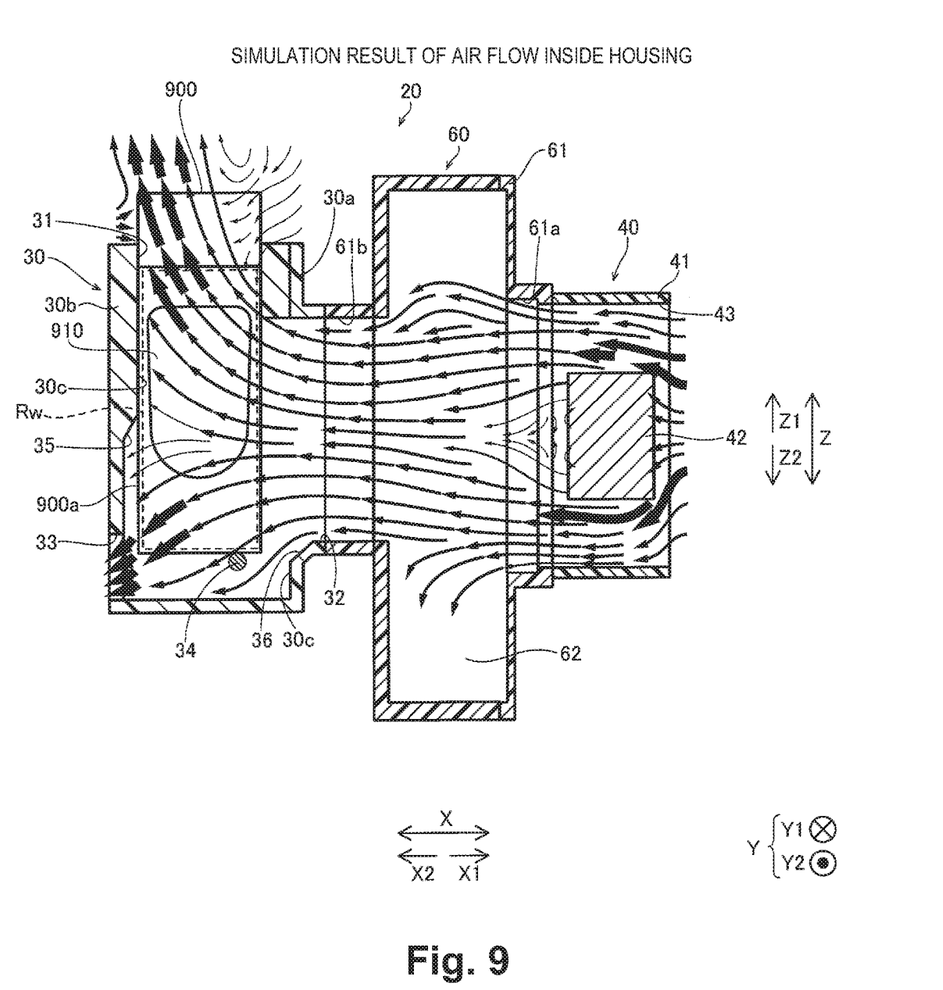
FIG. 9 is a simulation result of an air flow inside a housing.

Next, with reference to FIGS. 4 and 9, descriptions are provided for a simulation result of air flow inside housing 30.

Simulation conditions are determined as follows. The room temperature is set to 20° C. and the humidity is set to 30%. Housing 30 is set to house seven microscope slides 900. Setting is made such that a water film with a thickness of 0.1 mm exists on area Rw, which is to be soaked in dyeing liquid, of microscope slide 900 illustrated in FIG. 9. Note that area Rw includes smear portion 910. After blower 40 is operated for five minutes under these conditions, dryness of microscope slides 900 is evaluated. Note that in FIG. 9, a thicker arrow represents a faster flow speed, and a thinner arrow represents a slower flow speed. Fan 42 is illustrated as a rectangular shape for simulation.

It is confirmed that the air fed into feed opening 32 of housing 30 from heater 60 has a substantially uniform flow speed distribution over the entire area in the up-down direction near the connection portion between heater 60 and housing 30.

It is confirmed that the air fed into housing 30 hits against inner wall surface 30*c* on X2 side and branches into two directions, an upward flow and a downward flow.

It is confirmed that at insertion opening 31, air flow speed is larger on X2 side than that on X1 side.

It is confirmed that air flow speed is substantially uniform over the entire area in the up-down direction at discharge opening 33. It is confirmed that the air flow speed at discharge opening 33 is substantially equal to the air flow speed near X2 side of insertion opening 31.

It is confirmed that air passes through also near recess 35 because X2 side of inner wall surface 30*c* does not come in contact with side surfaces 900*a* of microscope slides 900.

It is confirmed that the air fed from blower 40 through feed opening 32 is guided near inclined portion 36 toward discharge opening 33.

It is confirmed that air passes through near shaft 34 and shaft 34 does not prevent air from passing through.

It is confirmed that after blower 40 is operated for five minutes, the first to fourth and the seventh microscope slides 900 from Y2 side out of seven microscope slides 900 (see FIG. 4) are completely dried. It is confirmed that on the fifth and the sixth microscope slides 900 from Y2 side out of seven microscope slides 900, an extremely small amount of water that does not drip remains. The amount of remaining water confirmed is at a level that does not cause the liquid to adhere to storage part 106 even if microscope slides 900 are stored in storage part 106.

As described above, it is confirmed that microscope slides 900 are mostly dried by the five-minute drying process.

One or more embodiments may be specified in the following paragraphs.

A smear preparing apparatus comprising:
 a transportation part that holds and transports a microscope slide;
 a housing defining a room therein, the housing comprising:
  an insertion opening through which the microscope slide transported by the transportation part is to be inserted, and
  a feed opening through which air is to be fed; and
 a blower configured to feed the air through the feed opening to the microscope slide housed in the housing,
  wherein the housing further comprises a discharge opening through which the air fed from the blower through the feed opening is discharged.

The smear preparing may further comprises a storage part that stores the microscope slide that is dried by the blower.

The transportation part may transport the microscope slide one by one from the housing to the storage part.

The smear preparing apparatus may further comprise a sample smear unit that smears a sample on the microscope slide.

The smear preparing apparatus may further comprises a dyeing unit that performs a dyeing process on a sample smeared on the microscope slide.

Note that it should be understood that the embodiments disclosed in this specification are illustrative and not restrictive in all aspects. The scope of the invention is defined not by the descriptions for the embodiments described above but by the claims, and includes all modifications within the scope of the claims and the equivalents thereof.

The invention claimed is:

1. A smear preparing apparatus comprising:
 a transportation part that holds and transports a slide;
 a housing defining a room therein, the housing comprising:
  an insertion opening through which the slide transported by the transportation part is to be inserted such that an upper end portion of the slide is exposed from the insertion opening outside the housing; and
  a feed opening of the housing through which air is to be fed; and
 a blower configured to feed the air through the feed opening to the slide to be housed in the housing;
 wherein
 the housing further comprises a discharge opening different from the insertion opening and the feed opening; and
 the air fed from the blower through the feed opening is discharged through the insertion opening and the discharge opening.

2. The smear preparing apparatus according to claim 1, wherein
 the insertion opening is formed at an upper end portion of the housing,
 the feed opening is formed at a first side of the housing, and
 the discharge opening is formed at one of: a lower end portion of the housing or at a second side of the housing, which is different from the first side of the housing.

3. The smear preparing apparatus according to claim 2, wherein the discharge opening is formed at a lower portion of the second side of the housing.

4. The smear preparing apparatus according to claim 2, wherein the discharge opening is formed at the second side of the housing that is provided opposite to the first side of the housing with respect to the room.

5. The smear preparing apparatus according to claim 1, wherein
the slide comprises a plurality of slides,
the housing is configured to house the plurality of slides, and
the transportation part sequentially pulls, from the housing, each of the plurality of slides that has stayed in the housing for a specified time and transports the respective pulled slide.

6. The smear preparing apparatus according to claim 1, wherein the blower is configured to feed the air through the feed opening toward a first edge side of the slide housed in the housing.

7. The smear preparing apparatus according to claim 1, wherein the housing is configured such that the air fed from the blower through the feed opening blows across a smear portion of the slide laterally from a first edge side to a second edge side of the slide, and is discharged from the discharge opening and the insertion opening.

8. The smear preparing apparatus according to claim 1, wherein at least a part of the feed opening is arranged between the insertion opening and the discharge opening in an up-down direction.

9. The smear preparing apparatus according to claim 1, wherein
the housing further comprises a first side and a second side, wherein the first side is arranged between the second side and the blower;
the first side comprises a first side portion adjacent to the feed opening, and
the second side of the housing comprises a second side portion including an inner wall surface that faces the feed opening.

10. The smear preparing apparatus according to claim 9, wherein
a lower portion of the inner wall surface of the second side of the housing includes a recess that is recessed from the inner wall surface toward an outer wall surface of the second side portion,
an edge side of the slide is adjacent to the second side of the housing,
a lower end portion of the recess is adjacent to the discharge opening, and
the recess is away from the edge side of the slide in a state in which the slide is housed in the housing.

11. The smear preparing apparatus according to claim 9, wherein
the housing further comprises a first inclined portion formed at the inner wall surface of the second side portion and a second inclined portion formed on the first side portion adjacent to a lower portion of the feed opening, and
the first inclined portion and the second inclined portion are inclined downward such that the air fed from the blower through the feed opening is guided toward the discharge opening.

12. The smear preparing apparatus according to claim 1, wherein the discharge opening is formed at a position where a lower end portion of the slide is exposed from the discharge opening in the state where the slide is housed in the housing.

13. The smear preparing apparatus according to claim 1, wherein
the slide comprises a plurality of slides,
the housing is configured to house the plurality of slides, and
the discharge opening has a width wider than a distance between a first slide at one end of the plurality of slides and a second slide at the other end of the plurality of slides in a direction in which the plurality of slides are arranged in the state where the plurality of slides are housed in the housing.

14. The smear preparing apparatus according to claim 1, wherein
the slide comprises a plurality of slides,
the housing configured to house the plurality of slides, and
the feed opening has a width wider than a distance between a first slide at one end of the plurality of slides and a second slide at the other end of the plurality of slides in a direction in which the plurality of slides are arranged in the state where the plurality of slides are housed in the housing.

15. The smear preparing apparatus according to claim 1, wherein
the slide comprises a plurality of slides,
the housing configured to house the plurality of slides, and
the housing further comprises a shaft configured to support lower end portions of the housed plurality of slides.

16. The smear preparing apparatus according to claim 1, wherein the feed opening is arranged at a position that overlaps with the slide, in a widthwise direction of the slide, in the state where the slide is housed in the housing.

17. The smear preparing apparatus according to claim 1, further comprising a heater arranged between the feed opening and the blower.

18. The smear preparing apparatus according to claim 1, further comprising a controller that controls operation of the blower on the basis of a housing state of the slide in the housing.

19. The smear preparing apparatus according to claim 1, further comprising a dyeing tub configured to store a dyeing liquid into which the slide with a sample smeared thereon is to be soaked.

20. The smear preparing apparatus according to claim 19, wherein the transportation part transports the slide from the dyeing tub to the housing.

\* \* \* \* \*